(12) United States Patent
Bergquist et al.

(10) Patent No.: US 7,381,667 B2
(45) Date of Patent: Jun. 3, 2008

(54) HYDROENTANGLED TEXTILE AND USE IN A PERSONAL CLEANSING IMPLEMENT

(75) Inventors: Paul Roland Bergquist, Southport, CT (US); Shauna Mary Lagatol, Westwood, NJ (US); Jesus Antonio Urbaez, Waterbury, CT (US); David Robert Williams, Monroe, CT (US); Gregory Aaron Grissett, Milford, CT (US); Filomena Augusta Macedo, Naugatucik, CT (US)

(73) Assignee: Unilever Home & Personal care USA, division of Conopco, Inc., Greenwich, CT (US)

( * ) Notice: Subject to any disclaimer, the term of this patent is extended or adjusted under 35 U.S.C. 154(b) by 790 days.

(21) Appl. No.: 10/645,885

(22) Filed: Aug. 21, 2003

(65) Prior Publication Data

US 2005/0191926 A1    Sep. 1, 2005

(51) Int. Cl.
D04H 1/46 (2006.01)
D04H 3/10 (2006.01)
D04H 5/02 (2006.01)
B32B 5/26 (2006.01)

(52) U.S. Cl. .................. 442/408; 442/57; 442/93; 442/381

(58) Field of Classification Search .................. 442/408, 442/381, 93, 57
See application file for complete search history.

(56) References Cited

U.S. PATENT DOCUMENTS

| | | | |
|---|---|---|---|
| 4,808,467 A * | 2/1989 | Suskind et al. ............. | 442/384 |
| 5,334,446 A | 8/1994 | Quantrille et al. | |
| 5,951,991 A * | 9/1999 | Wagner et al. ............... | 424/401 |
| 6,063,390 A | 5/2000 | Farrell et al. | |
| 6,110,848 A * | 8/2000 | Bouchette ................... | 442/384 |
| 6,280,757 B1 | 8/2001 | McAtee et al. | |
| 6,550,115 B1 * | 4/2003 | Skoog et al. ................. | 28/104 |
| 6,723,330 B2 * | 4/2004 | Bergquist ................... | 424/402 |
| 6,852,654 B2 * | 2/2005 | Fuller et al. ................ | 442/408 |
| 2003/0207632 A1 * | 11/2003 | Brooks ....................... | 442/164 |
| 2004/0068849 A1 | 4/2004 | Barge et al. | |

FOREIGN PATENT DOCUMENTS

| | | |
|---|---|---|
| EP | 0 308 320 | 9/1988 |
| EP | 0 418 493 | 7/1990 |
| EP | 0 534 863 | 9/1992 |
| EP | 1 126 066 | 1/2001 |
| WO | 00/18996 | 4/2000 |
| WO | 00/77286 | 12/2000 |
| WO | 01/08542 | 2/2001 |
| WO | 03/022230 | 3/2003 |

* cited by examiner

*Primary Examiner*—Norca Torres-Velazquez
(74) *Attorney, Agent, or Firm*—Milton L. Honig

(57) ABSTRACT

A non-woven hydroentangled textile is described formed in cross-section with a central area of low mass fiber density surrounded on both sides by areas of higher mass density. Further, a personal cleansing article is described wherein the hydroentangled textile is associated with a personal cleansing composition that includes a lathering surfactant. The composition is deposited onto, impregnated into or at least is partially enclosed by the textile. Also described is a process for producing the textile involving feeding into a hydroentangling unit a loose random assembly of fibers both above and below a fibrous screen modifying textile substrate.

19 Claims, 1 Drawing Sheet

HYDROENTANGLED TEXTILE AND USE IN A PERSONAL CLEANSING IMPLEMENT

BACKGROUND OF THE INVENTION

1. Field of the Invention

The invention concerns a new non-woven textile and use of this textile in a personal cleansing implement.

2. The Related Art

Hydroentanglement is a process utilized to form non-woven fabrics. The conventional process involves delivery of a loose, random assembly of relatively open fibers to a hydroentanglement unit via a series of fiber card machines. The loose, random assembly of fibers is conveyed through a series of high-velocity water jets aimed at curling and entangling the loose assembly of fibers about each other. Entanglement therefore provides strength and dimensional stability.

The primary method of structure development to achieve a surface texture occurs on a forming belt or screen onto which the loose fibers are deposited. These forming belts or screens are constructed of woven metal or plastic wires usually in plain weave configuration. For screens with large diameter wires, an open screen structure is created. Water jet forces onto the open screen structures at the wire intersections or knuckles move fiber away creating an opening or aperture in the subsequent non-woven structure. Open areas within the screen permit fiber entangling to occur. Hydroentanglement can either consolidate a fibrous web to impart strength, modify surface texture or act as both a web consolidation and surface texturing mechanism.

Certain types of personal care products require use of a non-woven substrate. These are applied to the skin delivering a lathering surfactant. In this context, there has been a need for a non-woven substrate with areas of low-mass fiber density surrounded by areas of greater-mass fiber density. In particular, a non-woven structure was sought based on a bonded fibrous assembly with improved coverage and loft.

SUMMARY OF THE INVENTION

A non-woven hydroentangled textile is provided formed in cross-section with a central area of low mass fiber density surrounded above and below (i.e. sandwiched) by areas of higher mass fiber density.

Furthermore, there is provided a personal care cleansing product formed from:
(i) a non-woven hydroentangled textile formed in cross-section with a central area of low mass fiber density surrounded above and below by areas of higher mass fiber density; and
(ii) a personal cleansing composition comprising lathering surfactant deposited onto, impregnated into or at least being partially enclosed by the textile.

Still further, there is provided a process for the manufacture of a non-woven hydroentangled textile which includes:
(i) feeding a fibrous screen modifying textile substrate into a hydroentangling unit;
(ii) feeding a loose random assembly of fibers into the hydroentangling unit, a portion of the assembly of fibers being deposited over and another portion of the assembly of fibers being deposited under the screen modifying textile substrate thereby forming a layered fibrous assembly;
(iii) applying a high velocity water jet to the layered fibrous assembly within the hydroentangling unit; and
(iv) transporting a resultant hydroentangled layered fibrous assembly to a drying area.

BRIEF DESCRIPTION OF THE DRAWING

Further features and advantages of the present invention will become more apparent from consideration of the drawing in which.

DETAILED DESCRIPTION OF THE INVENTION

Figure 1:
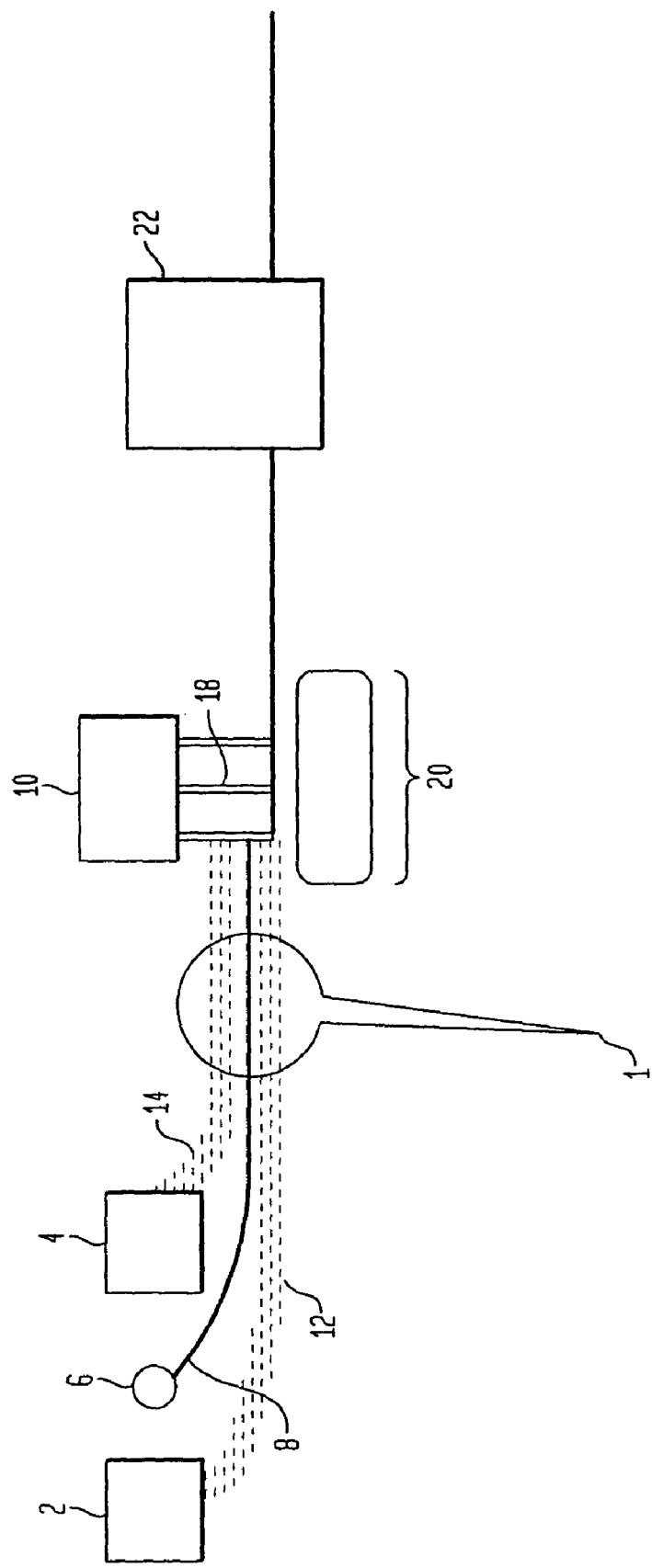
FIG. 1 is the sole FIGURE illustrating the process according to the present invention.

Now there has been developed a non-woven hydroentangled water-insoluble fabric which is a bonded fibrous assembly with improved coverage and loft. This textile has in cross-section an area of low mass fiber density (apertured) surrounded by areas of greater mass fiber density on either side. This modified hydroentangled arrangement is achieved by incorporating a screen modifying substrate in the normal hydroentangling process. In this system an apertured screen is utilized to obtain a non-apertured non-woven.

Conventional web formation techniques utilize a series of card machines to present a random loose fibrous assembly to the high velocity water jets. A screen modifying substrate labeled by some as a "scrim" according to the present invention is incorporated between two card machines. This results in a layered fibrous assembly comprised of both staple and continuous filament fibers. The presence of the fiber screen modifying substrate allows a certain amount of staple fibers to be entangled with a screen modifying substrate over the forming wire intersections (knuckles). This reduces the aperture forming capabilities of the forming belt or screen. Some embodiments may utilize four or more card machines and may even have more than one scrim.

The fibrous screen modifying substrate can be one comprised of randomly laid bonded continuous fibers. These fibers may be formed of polyethylene terephthalate (PET), polypropylene (PP), polyamide (PA), polyethylene (PE) and fiber combinations thereof. The fiber denier may range from about 0.1 to about 15, preferably from about 1 to about 7 denier. Substrate basis weight may range from about 5 to about 50 $g/m^2$, preferably from about 10 to about 25 $g/m^2$, optimally from about 12 to about 18 $g/m^2$.

A larger mass density above the screen modifying substrate improves product texture. The resultant non-woven structure is thereby comprised of areas of low-mass fiber density surrounded by areas of greater-mass fiber density. Larger mass density below the screen modifying substrate allows greater control in terms of aperture. The basis weight of loose, random assembly of fibers used above the screen modifying substrate may range from about 5 to about 100 $g/m^2$, preferably from about 20 to about 60 $g/m^2$, optimally from about 35 to about 45 $g/m^2$. Similarly, the basis weight of loose, random assembly of fibers used below the screen modifying substrate may range from about 5 to about 100 $g/m^2$, preferably from about 20 to about 60 $g/m^2$, optimally from about 35 to about 45 $g/m^2$. Advantageously the total amount of the basis weight of fiber deposited above and below the central area (screen modifying substrate) may range from about 20 to about 150 $g/m^2$, more preferably from about 30 to about 100 $g/m^2$, and optimally from about 40 to about 85 $g/m^2$. In a preferred embodiment the basis weight above and below the screen modifying substrate may range respectively in a ratio from about 3:1 to about 1:3, preferably about 2:1 to about 1:2, but optimally is substantially identical in a ratio of about 1:1.

Advantageously the amount of total basis weight (above and below the central area) to that of the screen modifying substrate may range from about 10:1 to about 1:2, preferably from about 6:1 to about 1:1, optimally from about 4:1 to about 2:1.

The hydroentangled textiles of the present invention may include a textured pattern, especially on an outer surface which has been in direct contact with the forming belt (screen). Peak to valley ratios may vary widely. Variation can be a function of the amount of loose random fibers deposited onto the scrim. Other factors include the degree of entanglement energy (water jet pressure against loose random fiber assembly applied prior to the hydroentangling unit) and the aperturing energy (water jet pressure within the hydroentangling unit). Still further, topography can be dependent upon the size of aperture openings within the forming belt (screen).

Forming belts or screens utilized during hydroentangling can be constructed of woven metal or plastic wires usually in plain weave configuration. Forming belts with open screen structures are incorporated during product manufacture. The degree of screen structure openings can be varied to modify product texture and form. Smaller screen structures (or openings) will decrease the variable mass fiber density obtained in product structures.

Water jet pressures during the hydroentanglement may range from about 50 to about 5000 psi, preferably from about 200 to about 3000 psi, optimally from about 1000 to about 2000 psi.

FIG. 1 illustrates the process for producing the non-woven textile according to the present invention. Card machines 2, 4 serve as a storage and dispensing reservoir of loose, random fibers (e.g. polypropylene). A delivery role 6 feeds a non-woven spunlaced web 8 serving as the fibrous screen modifying substrate. This substrate is fed into a hydroentangling unit 10. Simultaneously a stream of loose random fibers 12, 14 are delivered from respective card machines 2, 4 above and below substrate 8. Together the combination entering the hydroentangling unit 10 is a layered fibrous assembly 16.

Prior to entering the hydroentangling unit 10, optionally there may be a pre-entangling step wherein water jet pressure is applied to the layered fibrous assembly 16 in order to add strength thereto. Within the hydroentangling unit, the layered fibrous assembly 16 is subjected to a high velocity water spray from jets 18 as the layered fibrous assembly 16 is supported on a forming belt (screen) 20. The forming belt 20 then transports the hydroentangled layered fibrous assembly to a drying unit 22. Therein water is removed and the resultant hydroentangled textile is completed.

The non-woven textile of the present invention although constructed of a fibrous screen modifying substrate 8 and sandwiched between a random assembly of fibers 12, 14 is considered to be a single layered substrate. The reason is that subsequent to hydroentanglement, the textile cannot be separated into its component parts (i.e. substrate 8 and fibers 12, 14) without destruction of the textile. The basis weight for the textile of this invention may range from about 15 to about 200 g/m$^2$, preferably from about 60 to about 150 g/m$^2$, and optimally from about 80 to about 110 g/m$^2$.

For purposes of this invention, the fibrous screen modifying substrate 8 may be either a spunlace or a carded/ chemically bonded spunbond non-woven water-insoluble material. Sources for the substrate 8 can be spunbonded scrim available from Reemay Corporation of Tennessee, Superior Nonwovens of South Carolina, and PGI Corporation of South Carolina. The loft of textiles according to the present invention may range from a density of from about 0.00005 to about 0.1 g/cm$^3$, preferably from about 0.001 to about 0.09 g/cm$^3$ and a thickness from about 0.1 to about 5 cm.

As used herein, "non-woven" means that the layer does not comprise fibers which are woven into a fabric but the layer need not comprise fibers at all, e.g. formed films, sponges, foams or scrims. When the layer comprises fiber, the fibers can either be random (i.e. randomly aligned) or they can be carded (combed to be oriented in primarily one direction).

Textiles of the present invention may be utilized as implements in personal care cleansing products which may be appropriate for single use purposes. In these products, the textile may be impregnated or coated with a lathering surfactant and optionally skin conditioners. Representative of this technology are disclosures found in U.S. Pat. No. 6,280,757 (McAtee et al.), U.S. Pat. No. 5,980,931 (Fowler et al.), WO 00/42961 (Smith) and WO 01/08542 (Cen et al.), all herein incorporated by reference. Alternatively, the textile can be incorporated into a sachet with at least one wall of the sachet formed from a textile of the present invention and optionally other walls of the sachet formed from a variety of other water-insoluble woven or non-woven fabrics. A lathering surfactant and optionally conditioners may in dry particulate form be enclosed within the sachet. These products are exemplified and described in U.S. Pat. No. 6,063,390 (Farrell et al.) herein incorporated by reference.

An advantage of textiles according to the present invention in the context of personal cleansing sachets or pillows as described in U.S. Pat. No. 6,063,390 is that powdered surfactant and other powdered ingredients are prevented during dry storage from escaping through apertures in the textile. These apertures are sufficiently small to retain powder but sufficiently large to allow water to penetrate the sachet to activate surfactant and other ingredients (such as effervescent compounds) in the personal cleansing wash process. Additionally, the textile of the present invention on its outer surface exhibits a looser high loft structure with advantages for enhancing lathering of the surfactant and a softer feel when rubbed on the skin. A preferred embodiment of a personal cleansing article using the textile of the present invention is one which includes:

(i) an effervescent cleansing composition capable of generating foam upon contact with water; and (ii) a pouch formed of first and second water-insoluble substrates, at least one being water permeable, the first and second water-insoluble substrates forming therebetween an area housing the cleansing composition, and at least one of the substrates being a textile of construction according to the present invention.

Effervescent cleansing compositions which may be deposited into the pouch of the pillow includes a first component which is an acidic material and a second component which is an alkaline material. The acidic material is preferably citric acid and the alkaline material is preferably a bicarbonate such as sodium bicarbonate. Amounts of the acid and alkaline materials may each range from about 1 to about 80%, preferably from about 15 to about 40% by weight of the total composition within the sachet.

A wide variety of lathering surfactants may be used with the textile of this invention in any of its personal cleansing embodiments. Useful lathering surfactants include sodium lauryl sulfate, sodium lauryl ether sulfate, sodium lauroyl sarcosinate, sodium cocoyl taurate, sodium cocoyl isethionate, sodium alkyl amido propyl betaine, sodium $C_{14}$-$C_{16}$ olefin sulfonate, sodium lauryl sulfoacetate and any combinations thereof. The lathering surfactants may be of the anionic, cationic, nonionic, amphoteric, zwitterionic varieties and any combinations thereof. Amounts of the surfactant may range from about 0.1 to about 30%, preferably from about 1 to about 25%, optimally from about 8 to about 20% by weight of the total composition placed onto or in combination with the textile in personal cleansing products.

Conditioners whether water soluble or water insoluble or combinations thereof may be included in the composition used with the textile implement according to the present invention. Conditioners may be natural or synthetic esters, silicone oils, hydrocarbons, starches, fatty acids, cationic polymers and mixtures thereof. Typically the conditioners may range in amount from about 0.1 to about 35% by weight of the total composition.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

EXAMPLE

Personal cleansing pillows were constructed similar to those described in WO 03/022230, herein incorporated by reference. A powder similar to that described under Table II of the aforementioned patent application was placed as a powdered substance within the pouch of the pillows. A water-permeable wall of the aforementioned pillow was constructed with a non-woven hydroentangled textile according to the present invention. This Example correlates the Air Permeability of hydroentangled textile with different weight ratios of fiber for high (total above and below) to low mass fiber density areas and to evaluate Lather Release. For these experiments, the amounts of high mass density fiber was about equivalent in the areas above and below the low mass density fiber of the central area.

| Sample | Weight Ratio (high/low) | Total Weight (g/m$^2$) | Air Permeability* |
|--------|------------------------|------------------------|-------------------|
| I      | 3                      | 82                     | 266               |
| II     | 2.5                    | 71.5                   | 477               |
| III    | 1.5                    | 51                     | 678               |
| IV     | 4                      | 102                    | 371               |
| V      | 4.1667                 | 103                    | 348               |
| VI     | 2.875                  | 102                    | 250               |
| VII    | 3.375                  | 61                     | 529               |

*Measured according to ASTM D737-96.

Lather Release was measured in the following manner. A thermometer was attached to a sink faucet to read water temperature. The temperature of the water was then adjusted to 100° F. (38° C.) and maintained at that temperature. A sample pillow was taken in hand and placed in a stream of water for 3 seconds. The pillow was rotated in the hands so that both sides of the pillow would be exposed. Again the pillow was held in the water stream for another 3 seconds. As the pillow left the water stream, a timer was set to measure length of time required for full lather release. These times were noted and visual observations recorded. "Lather Release" was rated on the following scale:

Very good=0.2 seconds and represents full Lather Release instantaneously on both sides of the pillow; moderate billowing pressure should be noted;

Good=1-2 second with full Lather Release on both sides of the pillow;

Fair=2-4 seconds with slower Lather Release and different release rates seen from one side to another;

Poor=3-6 seconds with slow Lather Release, and high billowing internal pillow pressure.

The above procedure for each sample was repeated for 3-5 pillows of the same type. A combination of time and consensus from an expert panel based on the above procedure was utilized to provide the Lather Release description in the Table below.

| Sample | Air Permeability | Lather Release |
|--------|------------------|----------------|
| I      | 266              | Poor           |
| II     | 477              | Good           |
| III    | 678              | Very Good      |
| IV     | 371              | Fair           |
| V      | 348              | Fair           |
| VI     | 250              | Poor           |
| VII    | 529              | Very Good      |

Best Performance was achieved with Samples III and VII. These correlated with the highest level of Air Permeability. Consequently, the non-woven textile of the present invention should have a structure with an Air Permeability above 250, preferably at least 300 and optimally at least 500. The preferred range is from about 300 to about 1,000. It is to be noted that if the system becomes too Air Permeable, a powder held within the pillow would undesirably escape prior to being activated with water.

What is claimed is:

1. A non-woven hydroentangled textile formed in cross-section with a central area of low basis weight surrounded on both sides by areas of higher basis weight, the areas of higher basis weight being formed of fibers consisting of synthetic fibers, the textile having an Air Permeability ranging from 300 to 1000 and being incapable of separation in multiple layers after formation without destruction of the textile.

2. The textile according to claim 1 wherein the areas of higher basis weight on both sides in sum total relative to the central area of low basis weight has a basis weight ratio ranging from about 10:1 to about 2:1.

3. The textile according to claim 2 wherein the ratio ranges from about 6:1 to 2:1.

4. A personal cleansing article comprising:
   a) a non-woven hydroentangled textile formed in cross-section with a central area of low basis weight surrounded on both sides by areas of higher basis weight, the areas of the higher basis weight being formed of fibers consisting of synthetic fibers, the textile having an Air Permeability ranging from 300 to 1000 and being incapable of separation in multiple layers after formation without destruction of the textile; and
   b) a personal cleansing composition comprising a lathering surfactant deposited onto, impregnated into or at least being partially enclosed by the textile.

5. The article according to claim 4 wherein the lathering surfactant is present in amount from about 0.1 to about 30% by weight of the composition.

6. The article according to claim 4 wherein the personal cleansing composition further comprises from about 0.1 to about 35% by weight of a water-soluble or water-insoluble skin conditioning agent.

7. The article according to claim 4 wherein the personal cleansing composition further comprises effervescent ingredients capable of generating a foam upon contact with water.

8. The article according to claim 7 wherein the effervescent ingredients comprise an acid and a bicarbonate salt.

9. The article according to claim 4 wherein the areas of higher basis weight on both sides in sum total relative to the central area of low basis weight has a basis weight ratio ranging from about 10:1 to about 2:1.

10. The textile according to claim 1 wherein the areas of higher basis weight are formed of polypropylene.

11. The textile according to claim 1 within the areas of higher basis weight on both sides in sum total relative to the central area of low basis weight has a basis weight ratio ranging from 4:1 to 2:1.

12. The article according to claim 4 wherein the areas of higher basis weight are formed of polypropylene.

13. The article according to claim 4 wherein the areas of higher basis weight on both sides in sum total relative to the central area of low basis weight has a basis weight ratio ranging from 4:1 to 2:1.

14. The textile according to claim 1 wherein the area of low basis weight consist of fibers selected from the group consisting of polyethylene terephthalate, polypropylene, polyamide, polyethylene and fiber combinations thereof.

15. The article according to claim 4 wherein the area of low basis weight consist of fibers selected from the group consisting of polyethylene terephthalate, polypropylene, polyamide, polyethylene and fiber combinations thereof.

16. A non-woven hydroentangled textile formed in cross-section with a central area of low basis weight surrounded on both sides by areas of higher basis weight, the areas of higher basis weight being formed of fibers consisting of polypropylene, the textile having an Air Permeability ranging from 300 to 1000.

17. The textile according to claim 1 wherein the Air Permeability ranges from 500 to 1,000.

18. The article according to claim 4 wherein the Air Permeability ranges from 500 to 1,000.

19. The textile according to claim 16 wherein the Air Permeability ranges from 500 to 1,000.

* * * * *